United States Patent [19]  [11] Patent Number: 4,682,603
Franz  [45] Date of Patent: Jul. 28, 1987

[54] APPARATUS AND METHOD FOR RECORDING MONOPHASIC ACTION POTENTIALS FROM AN IN VIVO HEART

[76] Inventor: Michael R. Franz, Warburghof 12, 3000 Hannover 61, Fed. Rep. of Germany

[21] Appl. No.: 586,697

[22] Filed: Mar. 6, 1984

[51] Int. Cl.$^4$ ............................................. A61B 5/04
[52] U.S. Cl. .................................... 128/642; 128/696
[58] Field of Search ................ 128/642, 639, 734, 696

[56] References Cited

U.S. PATENT DOCUMENTS 4,172,451 10/1979 Kline .................................. 128/642

FOREIGN PATENT DOCUMENTS 730346 4/1980 U.S.S.R. ............................. 128/639

OTHER PUBLICATIONS

Gosling et al, "A Hand–Held Probe... Signals", J. Med Eng & Tech. (GB), vol. 3, No. 6, Nov. 1979, p. 299.
Pepper et al, "Manual ECG Electrode", Med & Biol Eng. & Comput. 1979, 17, 141.
Siegel et al, "Intracardiac Electrode . . . Ischemia", PACE, vol. 5, Nov.-Dec. 1982, pp. 892–902.
"A Simple and Safe Method for Intracardiac Recording of Monophasic Action Potentials in the Human Heart" (Franz, Pidgeon, Seed, Schottler and Schaefer).
"Simultaneous Recording of Monophasic Action Potentials and Contractile Force from the Human Heart" (Franz, Schottler, Schaefer and Seed).
"Further Improved Method for Measuring Monophasic Action Potentials of the Intact Human Heart" (Olsson, Varnauskas and Korsgren).
"The Monophasic Electrogram Obtained from the Mammalian Heart" (Jochim, Katz and Mayne).

Primary Examiner—Lee S. Cohen
Attorney, Agent, or Firm—Flehr, Hohbach, Test, Albritton & Herbert

[57] ABSTRACT

The apparatus comprises a probe having a tip portion, a first electrode mounted on a terminal free end of the tip portion and a second electrode spaced along the tip portion from the first electrode for supplying a reference potential. The probe is constructed so as to hold the first electrode in contact with tissue of an in vivo beating heart with a positive pressure without causing macroscopic damage to the heart tissue while orienting the probe such that the second electrode is spaced from the heart tissue. According to the method of the present invention, a plurality of monophasic action potentials can be obtained using the apparatus of the invention. The monophasic action potentials are used to identify abnormal heart areas, such as ischemic areas.

25 Claims, 13 Drawing Figures

APPARATUS AND METHOD FOR RECORDING MONOPHASIC ACTION POTENTIALS FROM AN IN VIVO HEART

BACKGROUND OF THE INVENTION

1. Field of the Invention

This invention relates to the recording of monophasic action potentials (MAPs) and more particularly to a method and apparatus for measuring MAPs by contacting heart tissue with a small electrode under positive pressure.

2. Discussion of Related Art

Studies have been performed on tissues obtained from human hearts. It has been learned that a resting cardiac cell has a transmembrane voltage difference of about 90 mV. The inside of the cell is negative relative to the extracellular fluid and, upon cell stimulation, an action potential ensues. The action potential consists of five phases. Phase 0 is rapid depolarization, phase 1 is early repolarization, phase 2 is the plateau phase, phase 3 is a rapid repolarization to the diastolic transmembrane voltage, and phase 4 is the diastolic period. The time-voltage course of the action potential varies among different cardiac cell types.

To examine the time course of local electrical activity under experimental conditions in which microelectrode recordings are difficult or impossible to make, such as in the vigorous beating in-situ heart, investigators have often used suction electrodes. The signal obtained with suction electrodes is monophasic and, although of smaller amplitude, accurately reflects the onset of depolarization and the entire repolarization phase of transmembrane action potentials recorded from cells in the same vicinity. Suction electrodes have also been used in human subjects, but the potential for subendocardial damage and S-T segment elevation has limited its clinical use to short recording periods of two minutes or less. Because the shape and duration of the action potentials vary from site to site in the heart, longer recording time from a single endocardial site is needed to evaluate long-term MAP changes, such as heart rate effects over several basic cycle lengths or in response to pharmacologic interventions.

SUMMARY OF THE INVENTION

An object of the present invention is to provide an apparatus for measuring monophasic action potentials.

A further object of the present invention is to provide a MAP measuring apparatus which can accurately record action potentials over sustained periods of time.

Another object of the present invention is to provide a MAP measuring apparatus which can measure action potentials on a vigorously beating in-situ heart.

Another object of the present invention is to provide a MAP measuring apparatus which, with slightly different modifications, may be employed to measure action potentials on both the endocardium and epicardium.

Yet another object of the present invention is to provide a method of using the apparatus for recording MAPs.

A further object of the present invention is to provide a method of detecting ischemia by sensing MAPs.

In accordance with the above objects, the present invention includes an apparatus for measuring monophasic action potentials in an in vivo beating heart. The apparatus comprises a probe having a tip portion and a first electrode mounted on a terminal end of the tip portion such that a portion of the first electrode is exposed to ambient. A second electrode is spaced along the tip portion from the first electrode for supplying a reference potential signal. The probe is provided with structure for holding the first electrode in contact with tissue of the heart with a positive pressure without causing significant macroscopic damage to the heart tissue and for orienting the probe such that the second electrode is spaced from the heart tissue.

In accordance with further aspects of the invention, a comparator is coupled to the first and second electrodes for subtracting signals received through the second electrode from the first electrode. The comparator is DC coupled to the electrodes and has a frequency response of approximately 100 Khz.

The electrodes are non-polarizable to avoid direct current drift during the course of investigation.

In accordance with further aspects of the invention, a flexible catheter may be used to hold the tip portion against heart tissue. The second electrode is exposed to ambient so as to contact fluid inside the heart. The fluid acts as a volume conductor to establish continuity between the second electrode and tissue adjacent that contacted by the first electrode. A guide wire may be disposed in the catheter to aid in directing the tip portion.

The probe may also include means for establishing electrical continuity between the electrodes and between the second electrode and tissue adjacent the tissue contacted by the first electrode. The continuity establishing means may comprise saline solution absorbed in foam material. The saline soaked foam replaces blood as a volume conductor.

The exposed surface of the first electrode may be approximately 1 mm across and the two electrodes are separated by a distance of approximately 3–5 mm.

The tip portion may also include an insulative material forming a raised ridge around the first electrode exposed portion, and the exposed portion of the first electrode may be generally planar.

The method according to the present invention comprises positioning the probe such that the first electrode is held against heart tissue with a positive force and such that the second electrode is spaced from the heart tissue. The method includes comparing signals from the first electrode to reference signals from the second electrode.

According to the method, the electrodes are short-circuited before contacting heart tissue by immersing the electrodes in a saline solution.

When the probe includes a flexible catheter, the positioning step of the method includes percutaneous catheter insertion.

The pressure applied to hold the first electrode in contact with heart tissue may be on the order of 20 to 30 g over the exposed area of the first electrode.

BRIEF DESCRIPTION OF THE DRAWINGS

The above and other objects of the present invention will become more readily understood from the following detailed description, reference being had to the accompanying drawings in which like reference numerals represent like parts throughout, and wherein.

DETAILED DESCRIPTION OF THE PREFERRED EMBODIMENTS

Figures 1, 2, 3, 4:
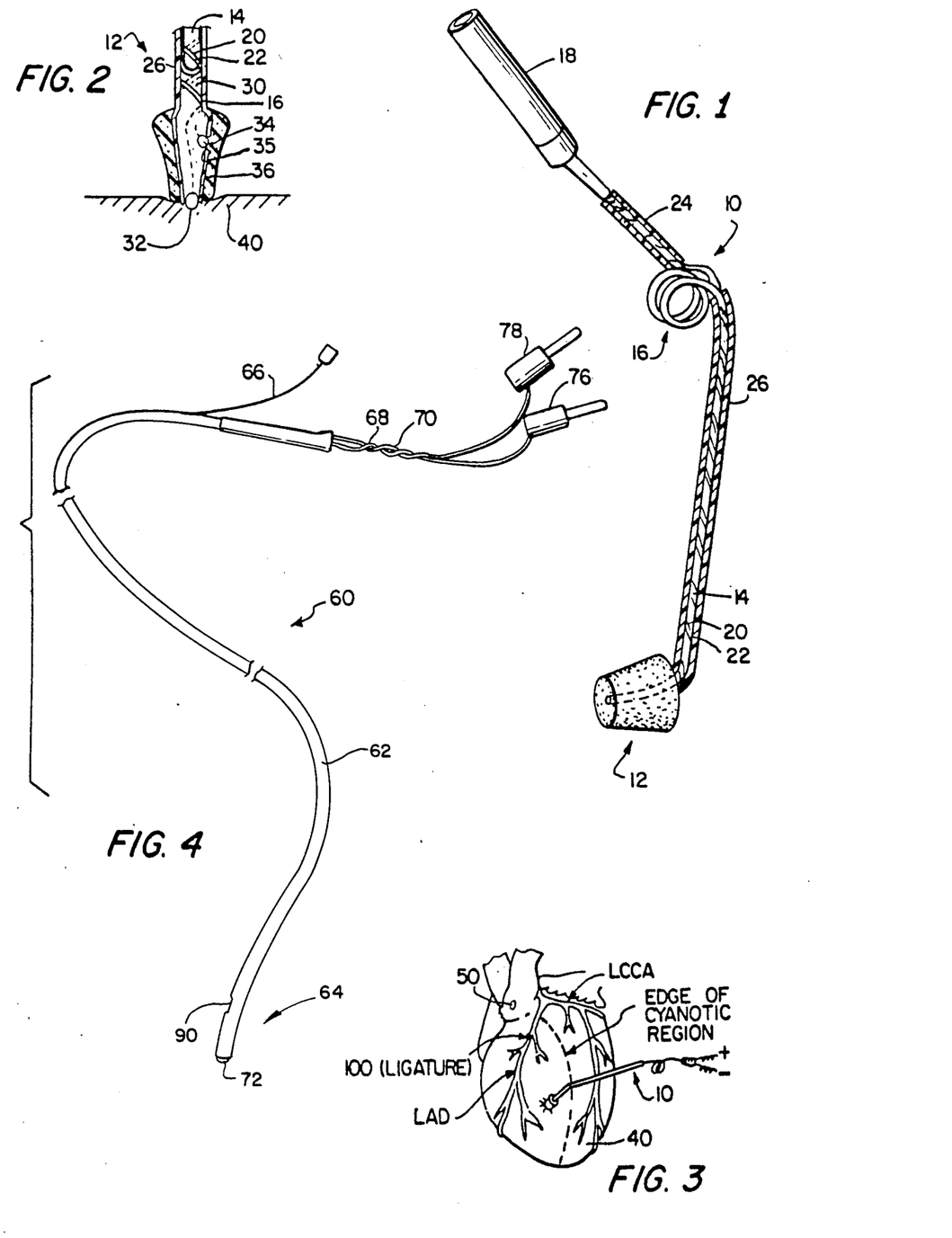
FIG. 1 is a perspective view of a measuring apparatus of the present invention for detecting monophasic action potentials on the surface of the epicardium.
FIG. 2 is an elevational sectional view of the tip portion of the apparatus of FIG. 1.
FIG. 3 is a schematic view showing the apparatus of FIG. 1 in operation.
FIG. 4 is a perspective part sectional view showing an apparatus of the present invention for measuring monophasic action potentials on the surface of the endocardium.

FIGS. 1 and 3 show a probe 10 according to the present invention. Probe 10 comprises a tip portion 12 which is connected to an end of a relatively stiff, flexible wire 14. The end of wire 14 attached to tip 12 is L-shaped. Wire 14 is also bent into two loops to form a spring section 16 and the opposite end of wire 14 attaches to a connector 18. A pair of electrical leads 20 and 22 are wrapped around wire 14. Leads 20 and 22 extend from the tip portion 12 to connector 18 and attach to terminals in connector 18. Connector 18 is a conventional electrical connector for making contact with leads extending to amplification and display circuitry, to be discussed hereinafter.

The portions of wire 14 above and below spring 16 are encased in plastic sheathing sections 24 and 26, respectively. Sheathing sections 24 and 26 are shown in sectional view only in FIG. 1.

Wire 14 can be conventional stainless spring steel wire which, combined with spring section 16, can produce a consistent force of approximately 20 to 30 g at the tip portion 12 when the tip portion is held against a rapidly beating in vivo heart. Sheathing 26 can be TEFLON tubing or the like, and connector 18 is a conventional electrical connector which receives leads 20 and 22.

FIG. 2 shows tip portion 12 in greater detail. Wire 14 terminates partway into the tip portion. Sheathing 14 is filled with epoxy resin 30 beyond the termination of wire 14. The epoxy resin is firmly attached to wire 14 and to the sheathing. A tip electrode 32 is embedded in the epoxy resin 30 at the extreme terminus of the tip portion 12. Electrode 32 is a silver-silver chloride pellet which protrudes to form a smooth spherical surface approximatley 1 mm in diameter. A proximal electrode 34 is also embedded in the epoxy resin 30 a distance of approximately 3-5 mm from tip electrode 32 along tip portion 12. Proximal electrode 32 is also a silver-silver chloride pellet approximately 1 mm in diameter. Proximal electrode 32 is accessible through an opening 35 in sheathing 26. Electrodes 32 and 34 comprise a non-polarizable matrix of silver-silver chloride. These electrodes are available in 1 mm pellets from In Vivo Metric Systems of California under the part no. E205.

Electrical wires 20 and 22 are connected, respectively, to electrodes 32 and 34 so as to provide electrical continuity between the electrodes and the terminals in connector 18.

Sheathing 26 is covered with a layer of foam rubber 36 which extends from above electrode 34 to a level approximately equal to electrode 32. The foam rubber is substantially cylindrically shaped and soaked with a 0.9% saline solution. The primary purpose of the foam rubber is to suspend the saline solution so as to provide electrical conductivity between proximal electrode 34 and tissue adjacent that which is contacted by tip electrode 32, as will be discussed hereinafter.

Now, with reference to FIGS. 2 and 3, an example of the use of probe 10 will be discussed.

Mongrel dogs weighing 20 to 30 kg were anesthesized by intravenous injection of sodium pentobarbital (25 mg/kg) or chloralose (60 mg/kg). Respiration was maintained with room air through a cuffed endotracheal tube by a Harvard respirator. The heart was exposed through left thoractomy and suspended in a pericardial cradle.

Probe 10 was positioned against the epicardium 40 such that tip electrode 32 contacted the epicardium with a force of approximately 20–30 g while the heart beat. The force was maintained by the spring steel wire 14 and spring 16 formed in wire 14.

Figure 9:
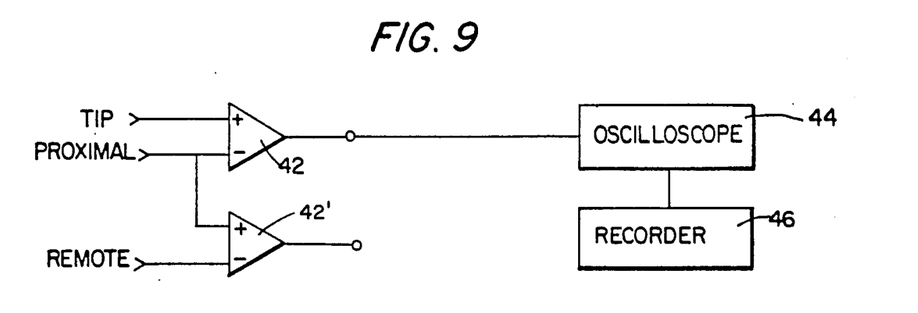
FIG. 9 is a schematic diagram showing the circuit connection of the apparatus of the present invention.

Epicardial MAP recordings were obtained by DC coupling the tip and proximal electrodes to a differential preamplifier 42, as shown in FIG. 9, with an input impedance of approximately $10^{11}$ ohms and a frequency range from direct current to 100 kHz. It should be noted that a preamplifier having a frequency range of direct current to approximately 5000 Hz should be sufficient for this application. The preamplified signal was displayed on a Tektronix storage oscilloscope 44 and written out on a multichannel photographic recorder 46.

The probe 10, either mounted or hand held, provided continuous MAP recordings of stable amplitude, smooth contour, and isopotential diastolic baselines over prolonged time periods from a single epicardial site. FIG. 10A shows an example of the epicardial MAP recordings. The arrow indicates the time at which contact pressure was applied. FIG. 10B shows the corresponding epicardial unipolar electrograms recorded by connecting the proximal electrode 34 of probe 10 to a second DC-coupled amplifier 42' (FIG. 9) and connecting a distant reference electrode 50 (FIG. 3) to the negative input of amplifier 42'. In FIGS. 10A and 10B, the first half of each graph was recorded at a speed of 10 mm/sec and the second half at a speed of 50 mm/sec.

The distant reference electrode 50 was provided by another silver-silver chloride electrode sewn into the aortic root. The stability of the 0-reference potential of the MAP recordings was checked at the beginning of each experiment and between interventions by comparing it with the diastolic potential recorded at the aortic root.

The exact mechanism underlying the genesis of the contact electrode MAP is not clearly understood. It is theorized that the MAP recordings were obtained by exerting pressure with the tip electrode 32 against a small region of epicardium 40. This likely depolarizes a number of myocardial cells such that they are no longer capable of participating actively in regenerative depolarization and repolarization. The magnitude and direction of local current flow, which results from the potential difference between the depolarized cells under the tip electrode 32 and the adjacent normal cells would determine the amplitude and polarity of the extracellular MAP recording. The magnitude of current flow, however, may not only depend on the difference in membrane potential between cells subjacent and adjacent the electrode tip. Other factors, such as the number of cells depolarized and therefore involved in generating current flow, the degree of electrotonic coupling of cells at the boundary of interest, and the conductance in the extra- and intracellular media surrounding the recording sight are likely to influence extracellular current flow and the amplitude of the MAP.

Referring again to FIG. 2, it should be understood that the purpose of the saline soaked foam rubber 36 is to provide a conductive path between proximal electrode 34 and the epicardium 40 surrounding tip electrode 32. In other words, the foam rubber acts as an extension of proximal electrode 34 but does not pressurize the epicardium and thus does not cause depolarization of the myocardium. The actual potential being measured appears to be that between the depolarized myocardium directly beneath the tip electrode 32 and the surrounding tissue.

FIG. 4 shows a catheter 60 used for bipolar measurements of MAPs from endocardial sites. Catheter 60 has a tip portion 64 which is shown in greater detail in FIG. 5. Tip portion 64 contains a tip electrode 72 and a proximal electrode 74. Cathether 60 comprises flexible tubing 62 which may be TEFLON or other durable material having a memory. Tubing 62 must be sufficiently flexible to be easily bent by the action of a beating heart, yet sufficiently resilient to maintain the tip portion 64 of the cathether in contact with the endocardium with a force estimated at approximately 20–30 g. A stainless steel guide wire 66 is inserted in the tubing 62 to improve the resiliency of the tubing and to aid in positioning the catheter tip portion 64. A pair of electrical leads 68 and 70 also extend through tubing 62 to make contact with tip electrode 72 and proximal electrode 74, respectively. The opposite ends of electrical leads 68 and 70 are connected to electrical connectors 76 and 78, respectively.

Figures 5, 7:
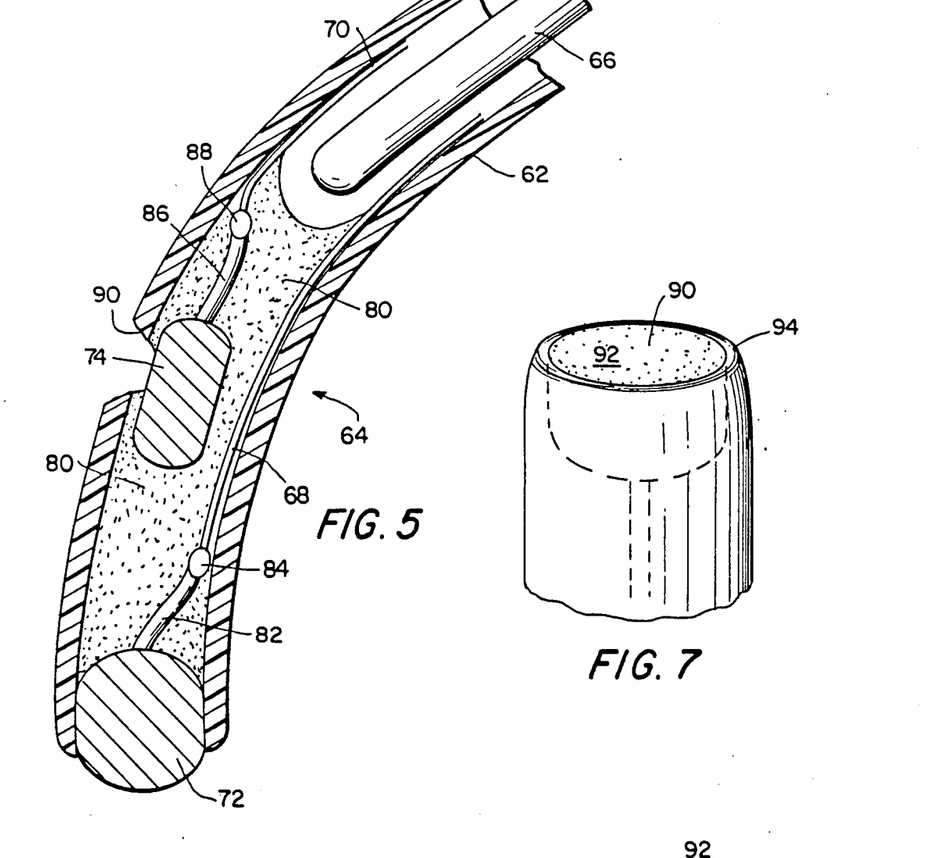
FIG. 5 is an enlarged sectional view of the tip portion of the apparatus of FIG. 4.
FIG. 7 is an enlarged view showing an improved tip electrode configuration.

As shown in FIG. 5, tip 64 is similar to tip 12 of probe 10 except that no foam rubber is provided around the tip. Tip electrode 72, which is a sintered silver-silver-chloride pellet of approximately 1 mm diameter, the same as tip electrode 32, protrudes from the terminal end of tip portion 64. Electrode 72 is held in place by epoxy cement 80. A silver wire 82 extends from tip electrode 72 and is soldered at point 84 to insulated lead 68. Similarly, proximal electrode 74, which is spaced about 5 mm upwardly along the tip portion 64 from electrode 72, is fixed in position by epoxy 80 and is connected to a silver wire 86 which is soldered at point 88 to insulated lead 70. The proximal electrode 74 is accessible through an opening 90 in tube 62 and is recessed somewhat within the catheter so that contact is made only with the outer medium (blood) in the heart and not the endocardium.

The tip and proximal electrodes of catheter 60 are connected to a preamplifier 42 (FIG. 9) through connectors 76 and 78 to provide oscilloscope and recorded readouts of the MAPs. A remote electrode can be placed in subcutaneous tissue remote from the heart, that is at the site of catheter insertion, to provide intracavitary electrograms.

Catheters have been employed having lengths from approximately 100–150 cm and a total outside diameter of approximately 1.3 mm. The spring steel guide wire may have a diameter of approximately 0.012–0.013 inches.

An example of the use of catheter 60 will now be set forth.

Before catheterization, electrodes 72 and 74 were immersed in sterile 0.9% saline solution for one hour with leads short-circuited to balance half-cell potentials. This procedure ensured that no appreciable direct current drift occurred during the course of the investigation. Diastolic baseline of intracavitary electrograms usually remain stable within ±1 mV during the entire recording time (1–3 hours). It should be noted that stainless steel or platinum electrodes conventionally used in clinical electrophysiology may produce considerable baseline drift of up to 160 mV during the first 30 minutes. After percutaneous catheter insertion by Seldinger technique and fluoroscopic positioning of the catheter within the heart, electrode leads were connected with sterile cables to the differential preamplifier 42. Firm approximation of the tip electrode to the endocardial surface was indicated by the recording of monophasic action potentials, which stabilized in amplitude and duration over a few beats.

Figure 6:
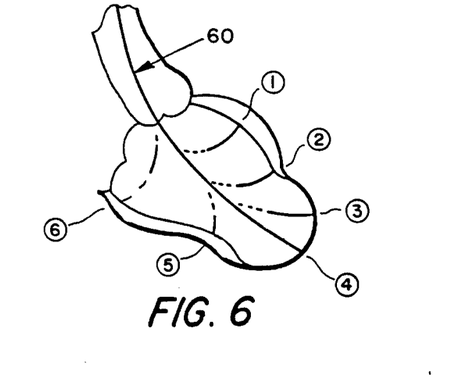
FIG. 6 is a schematic view showing the apparatus of FIG. 4 in operation.

FIG. 6 depicts the catheter 60 measuring MAPs at several different ventricular sites in a heart. The various sites are numbered 1 through 6 in FIG. 6. In each instance, positioning of the tip portion of the catheter was under fluoroscopic control.

Figure 8:
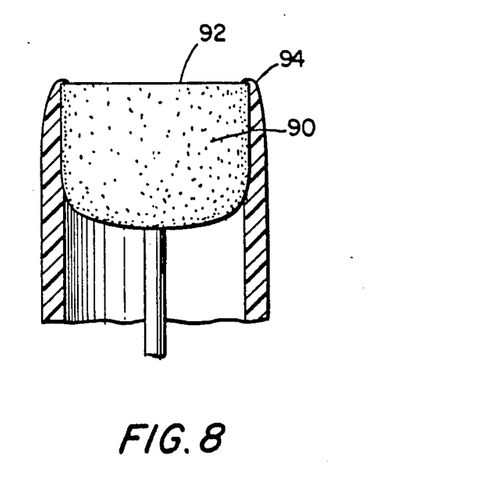
FIG. 8 is an elevational sectional view of the tip electrode configuration of FIG. 7.

FIGS. 7 and 8 show an alternate embodiment of a tip electrode 90 which can be used to replace either tip electrode 32 in probe 10 or tip electrode 72 in catheter 60. Tip electrode 90 is again sintered silver-silver chloride with an exposed surface diameter of approximately 1 mm. However, the exposed surface 92 is substantially planar and is surrounded by a small ridge 94 of insulating material. This tip design has proven to be most effective in producing long-term stable recordings of monophasic action potentials. The ridge 94 aids in sealing off contact of electrode 90 from the adjacent tissue and fluid. The design of the reference electrode is as before, i.e., it is mounted along the shaft 3-5 mm proximal from the tip.

The depth ridge 94 should only be approximately, 0.1 mm. The purpose of ridge 94 is to seal off electrode 90 from the surrounding tissue but not to prevent the electrode from pressurizing the myocardium. Electrode 90 must both produce the pressure and sense the voltage in the pressurized tissue. If the height of ridge 94 is too great, electrode 90 will be prevented from producing adequate pressure.

Ridge 94 creates a high resistance between the pressed tissue and the surrounding tissue. The thickness of ridge 94 should also not be too great so that the electrode is close to the boundary created by the ridge.

Referring again to FIGS. 1 and 4, it will be appreciated that the primary difference between probe 10 and catheter 60 is that probe 10 includes a saline soaked foam rubber piece 36. In probe 10, the saline solution acts as a volume conductor which establishes electrical continuity between the proximal electrode and the tissue surrounding the tissue pressed by tip electrode 32. With the catheter 60, the fluid (blood) within the heart itself is the volume conductor which serves this purpose. Therefore, no additional conductive material is required.

It should also be appreciated that with prior known suction electrode catheters, focal hemorrhage results at the site of suction within a few minutes. In contrast, no macroscopic damage to the tissue was seen in studies with the continuous contact electrode of the present invention. Furthermore, the stability of the contact electrode MAP over long recording periods may be considered indirect evidence that cellular alterations that lead to electrical uncoupling were minimal.

Thus, MAP recordings using the present invention appear to be safe and can easily be performed during routine cardiac catheterization along with other electrophysiologic measurements and pharmacologic interventions. MAPs recorded with the present invention can also provide a sensitive index of accute myocardial ischemia.

IDENTIFICATION OF ISCHEMIA/INFARCTION USING MONOPHASIC ACTION POTENTIALS

Figure 12:
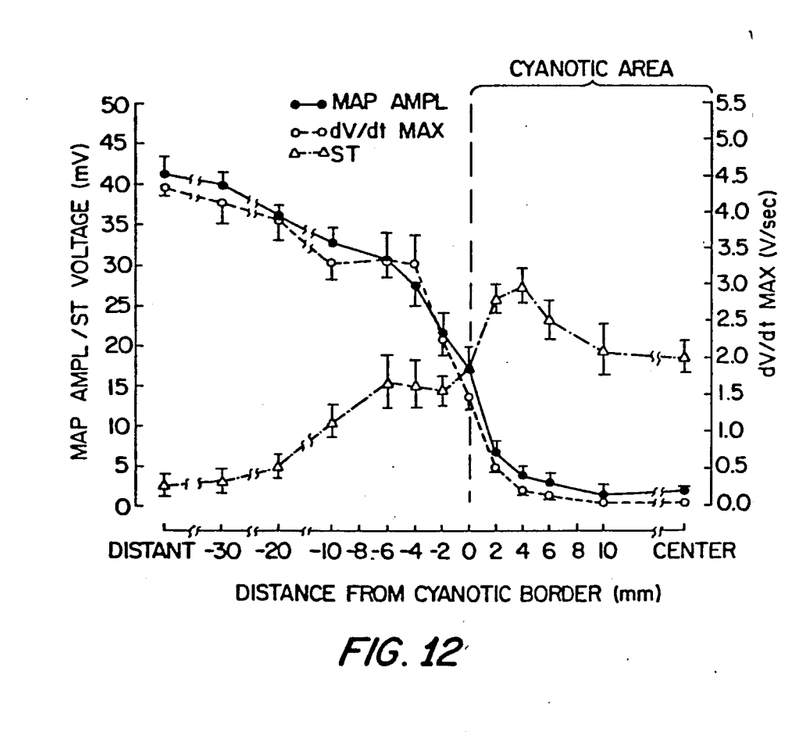
FIG. 12 is a graph of millivolts on the left and volts per second on the right versus distance showing mean values of monophasic action potential amplitudes, maximum derivatives, and total S-T segment voltages across the visible border of cyanosis from 465 recording sites in 7 dogs.

The ability to localize a region of myocardial ischemia by epicardial MAP recordings has been examined in 8 dogs and compared with standard epicardial S-T segment mapping. In order to produce transmural ischemia and infarction in a canine heart, the left anterior descending coronary artery (LAD) was permanently ligated proximal to the first diagonal branch and a biologically inert, non-resorbable polymer (dental rubber) injected into the arterial lumen. The ligation is shown on FIG. 3 at 100. This technique of vascular embolization, which extends into the arterioles, has previously been shown to create transmural infarcts with sharp histological borders in canine hearts. The white color of the injectate was also helpful in determining the vascular distribution of the LAD. Prior to ligation, 6 to 8 control measurements of the epicardial MAP and unipolar electrograms were made from defined locations inside and outside the anticipated ischemic region. Epicardial mapping was begun one hour after LAD occlusion and embolization and was completed within 15 minutes. The hand-held recording probe 10 was consecutively placed at multiple sites within, outside and near the border of the area of visible cyanosis. In each dog, measurements were made from 45 to 65 sites with an increased frequency of recordings close to the visible cyanotic border (shown in FIG. 3). The distance of the recording sites to the visible border of cyanosis was measured with a flexible ruler and recorded spatially on a map of the epicardial surface. For graphic presentation of mean data, the amplitude and dV/dt max of the MAP and the toral S-T segment voltage (T-Q depression plus "true" S-T elevation) were averaged in 2 mm intervals inside and outside the visible cyanotic border. This data is shown in FIG. 12, to be discussed hereinafter.

Figure 13:
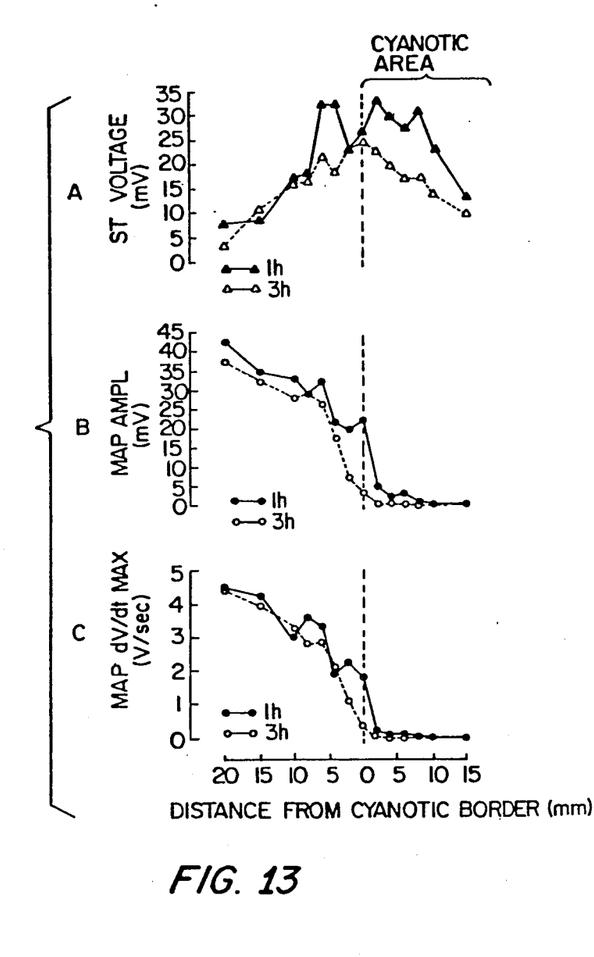
FIG. 13A is a graph of distance versus millivolts showing the effect of the duration of ischemia on S-T segment voltages recorded across a visible cyanotic border at intervals of 1 hour and 3 hours.
FIG. 13B is a graph of distance versus millivolts showing the effect of the duration of ischemia on monophasic action potential amplitudes at intervals of 1 hour and 3 hours.
FIG. 13C is a graph showing distance versus volts per second showing the effect of the duration of ischemia on maximum derivatives at intervals of 1 hour and 3 hours.

In order to assess the effect of duration of ischemia on the electrocardiographic measurements, epicardial mapping was repeated in 2 dogs, 3 hours after coronary artery ligation and embolization, at locations similar to the mapping study performed at one hour. The data obtained are shown in FIG. 13, also to be discussed hereinafter.

Figure 10:
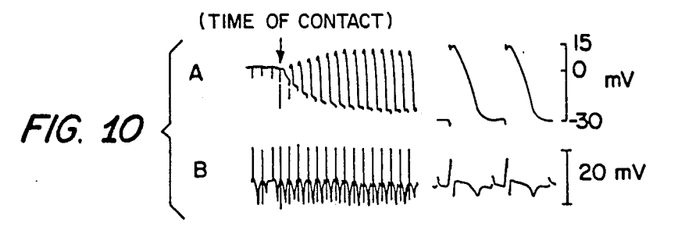
FIG. 10A is a graph of time versus millivolts showing actual recordings of MAPs from a nonischemic region.
FIG. 10B is a graph of time versus millivolts showing actual recordings of unipolar DC-coupled electrograms obtained simultaneously with the recordings of FIG. 10A from a nonischemic region.

In FIG. 10 are shown examples of MAP recordings (A) and standard unipolar electrograms (B) obtained from the epicardial surface of the canine left ventricle prior to ischemia. In general, MAP signals demonstrated "full" amplitude within 5 to 10 beats after stable contact of the electrode with the myocardial surface had been established. The time of contact is shown by the arrow in FIG. 10. Thereafter, MAP recordings remained stable in amplitude, $dV/dt_{max}$ and configuration for continuous recording periods of 1 hour or more. Using non-polarizable silver-silver chloride electrodes and DC amplification, it was possible to demonstrate a negative diastolic potential and a positive systolic potential with respect to the zero reference obtained from the diastolic baseline of the epicardial surface recording measured prior to application of significant contact pressure. Total amplitude of control MAPs recorded from the left ventricular epicardial surface ranged from 35 to 55 mV (42±4 mV, mean ±S.D.) which is considerably smaller than amplitudes previously reported for transmembrane action potentials (120 mV). In addition, the ratio of the positive voltage ("overshoot") to the total amplitude was greater in MAP than in intracellular recordings. The total MAP duration measured at 90% repolarization ($MAPD_{90}$) in 6 dogs was 192±12 msec and the duration of the plateau phase measured at 30% repolarization ($MAPD_{30}$) was 144±12 msec measured at a constant spontaneous heart rate of 120±5/min. Similar durations have been reported for transmembrane action potentials of canine ventricular myocardium.

Figure 11:
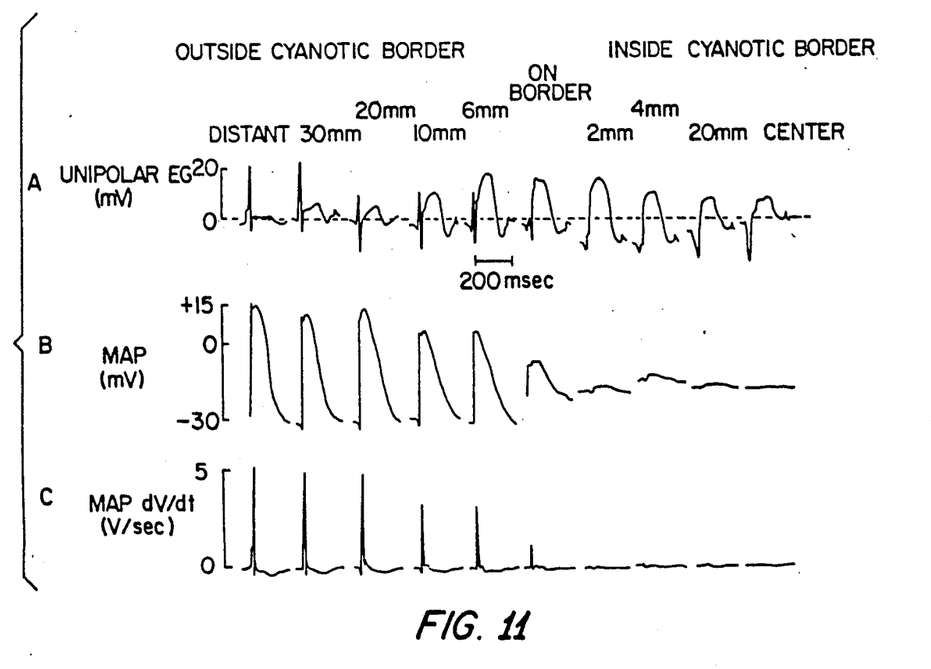
FIG. 11A is a graph of distance versus millivolts showing unipolar DC electrograms recorded at indicated distances from the visible border of cyanosis one hour after induction of ischemia/infarction.
FIG. 11B is a graph of distance versus millivolts showing monophasic action potentials taken simultaneously with the recordings of FIG. 11A.
FIG. 11C is a graph of distance versus volts per second showing the time derivatives of the monophasic action potentials of FIG. 11B.

To further examine the precision of MAP recordings for localizing regional myocardial ischemia, epicardial MAP recordings were made with the hand held probe 10 across the border of the region which was made transmurally ischemic by coronary artery ligation and distal embolization with dental rubber, as discussed above. FIG. 11 shows original MAP recordings (B), their first time derivative (dV/dt) (C) and adjacent, simultaneously recorded unipolar epicardial electrograms (A) at various distances from the cyanotic border one hour after induction of transmural ischemia/infarction. MAPs recorded 20 mm or more outside the visible border of cyanosis had amplitudes, durations, configurations and $dV/dt_{max}$ values comparable to those recorded at distant sites and comparable to those recorded at the same site prior to occlusion. Epicardial MAPs recorded from sites 10 mm or less outside the cyanotic border demonstrated noticeable decreases in plateau amplitude and duration and decreases in the slope of the final repolarization phase (phase 3), resulting in a more triangular shaped MAP with a greater total duration. Values of $dV/dt_{max}$ were also noted to be decreased at these sites. As the MAP recording probe was moved across the cyanotic border, MAP amplitude decreased sharply and $dV/dt_{max}$ values approached zero 2 mm inside the border. The decrease in MAP amplitude was due to a loss in both diastolic (negative) and systolic (positive) potential. In the center of the ischemic region, nearly isopotential recordings at negative potentials ranging from $-15$ to $-5$ mV were obtained. In contrast, epicardial S-T segment voltages were highest just inside the cyanotic border decreasing progressively toward the center of the ischemic region. As seen in FIG. 11A, these increases in total S-T segment voltage were due to a combination of "true" S-T elevation and T-Q segment depression. The relative contribution of T-Q segment depression, however, was greater in recordings inside the ischemic region (where MA recordings demonstrated markedly reduced diastolic potentials). In contrast, outside the cyanotic border, true S-T segment elevation contributed the largest portion of the total S-T segment change.

In FIG. 12 are summarized MAP and total S-T segment recordings made in 8 dogs across the lateral border of cyanosis 1 hour after induction of transmural ischemia. Unipolar epicardial electrograms demonstrating significant S-T segment elevations (27±6 mV) were recorded 4 mm inside the cyanotic border. In epicardial electrograms recorded near the center of the ischemic region, both T-Q and S-T segment displacements were found to be lower in magnitude than those recorded just inside the border. Total S-T segment voltages in these more central ischemic regions (16–22 mV) were not significantly different in magnitude from those measured 4–6 mm outside the border (p. 13). Unipolar electrograms recorded in the center of the ischemic region did differ from those recorded just outside the border, however, by the presence of diminished R wave voltage and/or the presence of Q waves (FIG. 11). In particular, in FIG. 12, the uniform loss in MAP amplitude and dV/dt throughout the ischemic region should be noted. This is in contrast to the decline in S-T segment voltage towards the center of the ischemic region.

The distribution of blood flow across the lateral border of the cyanotic region was determined in 6 dogs using the radioactive microsphere technique. Myocardial blood flow was 1.42±0.35 ml/min/g in the subepicardial layers and 0.65±0.28 in the subendocardial layers 2–4 mm outside the visible edge of cyanosis and decreased to, 0.01±0.05 and 0.01±0.02 2–4 mm inside the cyanotic border. These flow data confirm that the technique used to produce transmural infarction in a canine heart resulted in a sharp lateral border of ischemia with a transition from normal to zero blood flow over a width of only 6 mm.

The influence of the duration of ischemia on the transition of MAP and corresponding S-T segment recordings across the cyanotic border was studied in 3 additional dogs. These results are shown in FIG. 13. Measurements of MAP amplitude and $dV/dt_{max}$ repeated 2 hours after the initial mapping study demonstrated near zero values even closer to the edge of the cyanotic border than after 1 hour of ischemia as well as further reductions just outside the border. In contrast, epicardial S-T segment elevations demonstrated an overall decrease in magnitude over the same time period, making localization of the border even less well defined.

The local epicardial S-T segment voltages recorded using probe 10 are consistent with previous reports of the ability of epicardial S-T segment mapping to delineate a region of ischemia. S-T segment elevations were found 20 mm or more outside the cyanotic border and reached maximum values just inside the border. As also demonstrated in previous studies, S-T segment voltages decreased towards the center of the ischemic area such that the magnitude of S-T segment elevations recorded in the central ischemic region was not significantly different from those recorded at sites 5 to 10 mm outside the area of reduced flow. The wide zone of transition of epicardial S-T segment voltage across the border and the loss of S-T segment voltage in the center of the ischemic region are expected on theoretical grounds. S-T segment displacements are caused by current flow between normal and ischemic myocardium. Potential gradients and thus injury current flow are less between adjacent ischemic regions than between ischemic and normal regions resulting in greater S-T segment voltages closer to the ischemic border than in the center of the ischemic area. In contrast, loss of epicardial MAP amplitude and $dV/dt_{max}$ were found to be uniform throughout the ischemic region, thus correlating better with the absence of flow.

The transition from nearly absent to nearly normal MAP recordings across the cyanotic border occurred over a distance of less than 8 mm. This electrical transition was slightly greater in width than the flow transition which had a width of approximately 6 mm. The width of the border "zone" over which transition in flow, metabolism or electrophysiologic variables are detected depends on the resolving power of the techniques employed to measure these variables. The finding of intermediate values for flow, metabolites or electrophysiological changes could result from measurements obtained either from a mixture of normal and ischemic cells or from a uniform composition of cells with an intermediate degree of change. The slightly wider transition for MAP changes, as compared to the flow transition, may indicate a limit to the resolving power of MAP recordings or may reflect scatter related to microsphere flow measurements being made from 2 mm wide tissue samples. On the other hand, abnormal MAPs recorded just outside the cyanotic border do not necessarily indicate that the tissue recorded from is injured. Current flow between ischemic and nonischemic tissue may decrease the amplitude and rise velocity of transmembrane action potentials in nonischemic cells.

A decrease in the magnitude of S-T segment voltages with duration of ischemia (see FIG. 13) has been documented in both experimental and clinical studies. It has been reported that epicardial and intramural S-T segment potentials in the porcine heart reach maximal values 7 to 15 minutes after coronary artery ligation and then decrease with time despite a progressive deterioration of the metabolic situation. Substantial reduction in S-T segment elevation in patients over the first 24 hours following acute myocardial infarction has been reported as part of the natural history of myocardial infarction. This discrepancy between S-T segment voltage and metabolic and histologic deterioration has been explained by progressive electrical uncoupling between damaged and normal myocardial cells so that, despite a persistent electrical gradient, flow of injury current decays and eventually ceases. In contrast, ischemia-induced loss of MAP amplitude and $dV/dt_{max}$ persists or becomes even more pronounced three hours after coronary artery occlusion and distal embolization than after one hour. This indicates that the information on ischemic injury obtained from MAP recordings is not compromised by electrical uncoupling as is the ECG, and suggests that MAP recordings can be used not only as a more precise but also more reliable electrophysiologic index for defining the spatial extent of ischemic/infarcted myocardium.

In general, the apparatus and method of the present invention can be used to detect ionic imbalance due to a change in electrolyte balance in the heart as well as ischemia due to a reduction in blood flow.

Monophasic action potentials (MAPs) have hitherto mostly been recorded with suction electrodes. However, the "contact electrode" technique of the present invention provides more stable MAP recordings than suction electrodes and has been shown to also allow safe, long-term MAP recordings in human subjects without tissue injury. Endocardial and epicardial MAP recordings using the present invention have been found to resemble transmembrane action potentials and, following the induction of regional ischemia or changes in potassium ion concentration, undergo changes similar to those previously reported in intracellular recordings. Localization of a region of myocardial ischemia by MAP mapping is more accurate and less dependent on the duration of the ischemic process than S-T segment mapping. Endocardial MAP mapping in the cardiac catheterization laboratory and both epicardial and endocardial MAP mapping in the cardiac operating room should permit the identification of sites of regional ischemia in man and to assess the acute effects of therapeutic interventions designed to reduce the severity of an ischemic insult.

The foregoing description is set forth for the purpose of illustrating the present invention. However, it should be apparent that numerous changes can be made in the invention without departing from the scope thereof, as set forth in the appended claims.

What is claimed is:

1. An apparatus for measuring monophasic action potentials in an in vivo beating heart, comprising:
   a probe having a tip portion;
   a first electrode mounted on a terminal free end of said tip portion, said first electrode having a portion exposed to ambient;
   a second electrode spaced along said tip portion from said first electrode for supplying a reference potential signal; and
   means on said probe which is spring loaded for holding said first electrode in contact with tissue of a beating heart with a positive force of approximately 20–30 g without causing macroscopic damage to said heart tissue and orienting said probe such that said second electrode is spaced from said heart tissue.

2. An apparatus as claimed in claim 1, further including comparator means coupled to said first and second electrode for subtracting signals received through said second electrode from said first electrode.

3. An apparatus as claimed in claim 2, wherein said comparator means is DC coupled to said first and second electrodes and has a frequency response from DC to approximately 5 kHz.

4. An apparatus as claimed in claim 1, wherein said electrodes are nonpolarizable.

5. An apparatus as claimed in claim 1, wherein said holding means comprises a flexible catheter, and said second electrode is exposed to contact fluid in the heart.

6. An apparatus as claimed in claim 5, including a guide wire disposed in said catheter.

7. An apparatus as claimed in claim 1, including means for establishing electrical continuity between said second electrode and tissue surrounding tissue contacted by said first electrode.

8. An apparatus as claimed in claim 7, wherein said holding means comprises a spring built into said probe.

9. An apparatus as claimed in claim 7, wherein said continuity path establishing means comprises saline solution.

10. An apparatus as claimed in claim 7, wherein said continuity path establishing means does not apply significant pressure to the tissue it contacts.

11. An apparatus as claimed in claim 1, wherein said first elecrode has an exposed surface on the order of approximately 1 mm across.

12. An apparatus as claimed in claim 1, wherein said electrodes are separated by a distance on the order of approximately 3–5 mm.

13. An apparatus as claimed in claim 1, wherein said exposed portion of said first electrode is generally planar.

14. An apparatus as claimed in claim 13, wherein said tip portion includes an insulative material forming a raised ridge around said first electrode exposed portion.

15. An apparatus as claimed in claim 1, wherein both said electrodes comprise silver-silver chloride.

16. An apparatus for measuring monophasic action potentials in an in vivo beating heart, comprising:
   a probe having a tip portion;
   a first electrode mounted on a terminal free end of said tip portion, said first electrode having a portion exposed to ambient;
   a second electrode spaced along said top portion from said first electrode for supplying a reference potential signal;
   means on said probe for holding said first electrode in contact with tissue of a beating heart with a positive pressure without causing macroscopic damage to said heart tissue and orienting said probe such that said second electrode is spaced from said heart tissue, said holding means comprising a spring built into said probe; and
   means for establishing electrial continuity between said second electrode and tissue surrounding tissue contacted by said first electrode, said continuity establishing means comprising saline solution and a foam material on said tip portion, said saline solution being received in said foam material.

17. A method of measuring monophasic action potentials in an vivo heart using a probe having a spring loaded portion and having a tip portion with a first electrode at an extremis of said tip portion, and a second electrode spaced along said probe from said tip portion, comprising:
   positioning said probe such that said first electrode is held against heart tissue and said spring loaded portion maintains a positive force on the order of 20–30 grams over the exposed area of said first electrode and said second electrode is spaced from said heart tissue; and comparing signals from said first electrode to reference signals from said second electrode.

18. A method as claimed in claim 17, including the preliminary step of short-circuiting said electrodes to balance half cell potentials.

19. A method as claimed in claim 18, wherein said electrodes are short-circuited by immersing said electrodes in saline solution.

20. A method as claimed in claim 17, wherein said probe includes a flexible catheter and said positioning step includes percutaneous catheter insertion.

21. A method of detecting an abnormal heart condition using a probe having a spring loaded portion and having a tip electrode comprising:

measuring monophasic action potentials of a plurality of sites on the surface of said heart by pressing said tip electrode against said heart surface at each of said sites using said spring loaded portion to maintain a positive pressure on the order of 20 to 30 grams, comparing a signal received by said tip electrode against a reference potential and recording a monophasic action potential; and identifying abnormal heart areas by comparing recorded monophasic action potentials against one another and identifying monophasic action potentials which have a reduced amplitude relative to other monophasic action potentials, said reduced amplitude monophasic action potentials being associated with abnormal heart areas.

22. A method as claimed in claim 21 including the steps of forming a first time derivative of each recorded monophasic action potential and identifying abnormal heart areas as areas associated with monophasic action potentials having a reduced maximum first derivative.

23. A method as claimed in claim 21, including measuring said reference potential using an electrode in electrical continuity through a volume conductor with tissue adjacent tissue against which said tip electrode is pressed.

24. A method as claimed in claim 23, wherein said volume conductor is formed of body fluids and said tip electrode is pressed against the surface of the endocardium.

25. A method as claimed in claim 23, wherein said volume conductor is formed of saline solution and said tip electrode is pressed against the epicardium.

* * * * *